United States Patent

Frye et al.

[11] 4,107,196
[45] Aug. 15, 1978

[54] N-TERTIARYBUTYL ORGANOSILYLAMIDES

[75] Inventors: Cecil L. Frye; Thomas H. Lane, both of Midland, Mich.

[73] Assignee: Dow Corning Corporation, Midland, Mich.

[21] Appl. No.: 858,144

[22] Filed: Dec. 7, 1977

[51] Int. Cl.² .................................... C07F 7/10
[52] U.S. Cl. ............................. 260/448.2 N
[58] Field of Search .................... 260/448.2 N

[56] References Cited

U.S. PATENT DOCUMENTS

| | | | |
|---|---|---|---|
| 2,876,209 | 3/1959 | de Benneville et al. | 260/448.2 N X |
| 2,876,234 | 3/1959 | Hurwitz et al. | 260/448.2 N X |
| 2,906,756 | 9/1959 | de Benneville et al. | 260/448.2 N X |
| 3,776,933 | 12/1973 | Toporcer | 260/448.2 N X |
| 3,954,651 | 5/1976 | Donike | 260/448.2 N X |
| 3,488,371 | 1/1970 | Klebe | 260/448.2 N |

*Primary Examiner*—Paul F. Shaver

*Attorney, Agent, or Firm*—Robert F. Fleming, Jr.

[57] ABSTRACT

N-tertiarybutyl silylamides of the formula

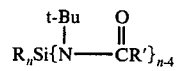

where $n$ is 2 or 3, are extremely rapid silylating agents and are especially good for silylation in connection with the separation of complex mixtures. A typical compound is

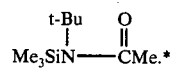

*In this application the following abbreviations are used: t-Bu for the tertiarybutyl radical, Me for the methyl radical, Et for the ethyl radical, Vi for the vinyl radical, Ph for the phenyl radical and i-Pr for the isopropyl radical.

5 Claims, No Drawings

N-TERTIARYBUTYL ORGANOSILYLAMIDES

BACKGROUND OF THE INVENTION

Silylamides are known from U.S. Pat. No. 2,876,209 which shows the preparation of amidosilanes by reacting an aminosilane of the formula $R_{4-x}Si(NR'R'')_y$, with amides with the removal of the amine by-product by volatilization. The amidosilanes produced are of the formula

where R' can be alkyl of 1 to 18 carbon atoms such as methyl, ethyl, butyl, etc. However, this patent has no specific disclosure of an N-t-butylamide either in column 4, line 52, or lines 58–68 where the various groups substituted on the nitrogen are elucidated. A t-butyl-silylamine is one of the starting materials but the t-butyl group is removed as t-butyl amine by volatilization.

A similar disclosure appears in U.S. Pat. No. 2,876,234 which claims the amidosilanes. U.S. Pat. No. 3,436,415 discloses the compound allylethylbis-N-isopropyl-propionamidesilane, column 2, line 39, and its use as an intermediate in the preparation of silyloxazolidones. Also U.S. Pat. No. 3,488,371 discloses the compound phenylmethylbis-N-(beta-phenylisopropyl)acetamidosilane (Example 5). None of these references, however, disclose the N-t-butyl derivative of these amidosilanes.

It is also known that amidosilanes and various other reactive silanes are silylating agents which are extensively used in reaction with organic or inorganic molecules containing the hydroxyl, the NH or the SH group. In general, these silylations are carried out in order to modify the starting compounds either in order to carry out additional synthetic steps or in order to modify complex mixtures so that they can be more easily separated. Additional reasons for silylation are to modify surfaces of materials in order to render them hydrophobic and organophilic.

It is the object of this invention to prepare novel silylamides which are much more reactive silylating agents than the best previously known silylating agent which is bis-(trimethylsilyl)acetamide. This compound silylates quite rapidly, but usually only one of the trimethylsilyl groups are employed. The by-product is N-trimethyl-silylacetamide so one half of the potential silylating groups are not used. The compounds of this invention are some 5 times faster than the bis-trimethyl-silylacetamide (BSA) and all of the silicon is used during the silylation.

The compounds of this invention can be used for silylating any compound containing the OH, NH, SH or carboxyl group. They are particularly useful in silylating unreactive compounds such as ureas and in the silylation of complex mixtures.

BRIEF DESCRIPTION OF THE INVENTION

This invention relates to compounds of the formula

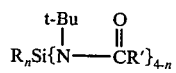

where n is 2 or 3, R is of the group methyl, ethyl, vinyl, phenyl or 3,3,3-trifluoropropyl at least 2 R's being methyl when n is 3 and R' is methyl or ethyl.

GENERAL DESCRIPTION OF THE INVENTION

It should be understood that the compositions of this invention are more complex than the simple formula shown above. It is generally believed that silylated amides are actually an equilibrium mixture of tautomeric materials represented by the equation

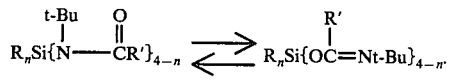

In other words, it is believed that the compounds are mixtures of the amide and imidate form of these materials. Consequently, it should be understood that this application and the claims in this application cover both forms of the molecules and mixtures thereof.

The compositions of this invention where n is 3 are best prepared by reacting the chlorosilane of the formula $R_3SiCl$ with the corresponding N-t-butylamide in the presence of a tertiary amine as a hydrogen halide acceptor. This reaction proceeds readily at room temperature and the amine hydrochloride salt is removed by filtration or other suitable means and the silylated amide is obtained by distillation or other suitable means. The compositions of this invention where n is 2 are best prepared by reacting a silane of the formula $R_2SiCl_2$ with the corresponding compound

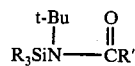

under conditions where the triorganochlorosilane is removed from the reaction zone. This reaction will generally occur at ambient temperature and the $R_3SiCl$ can be removed at reduced pressure.

The following examples are illustrative only and should not be construed as limiting the invention which is properly delineated in the appended claims.

EXAMPLE 1

A dry flask was fitted with a reflux condenser, stirring bar and septum and evacuated and flushed with dry nitrogen. The flask was protected from moisture with nitrogen and a series of dry ice traps. The flask was charged with 20 g. of sublimed N-t-butylacetamide, 118.39 g. of triethylamine and 50 ml. of dry pentane. 37.73 g. of trimethylchlorosilane was added to the stirred solution through a syringe. A slight exotherm was noted along with the precipitation of triethylamine hydrochloride. The mixture was allowed to stir overnight and the slurry was centrifuged. The organic liquid was filtered and the salts washed with dry pentane. The combined organic liquids were distilled to give a 61.7 percent yield of

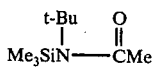

boiling at 62° C at 22 mm of mercury. The structure of the compound was verified by infrared analysis and nmr analysis.

EXAMPLE 2

The relative reactivity of the various N-alkyl substituted trimethylsilylacetamides was determined by reacting each with N-butylacetamide. This reaction goes in accordance with the following equation:

$$\underset{A}{Me_3SiN(Y)-C(O)Me} + \underset{B}{HN(Bu)-C(O)Me} \rightleftarrows \underset{C}{HN(Y)-C(O)Me} + \underset{D}{Me_3SiN(Bu)-C(O)Me}$$

The amount of D produced at equilbrium is a measure of the reactive reactivity of A with respect to D and the reactivity of A is a function of the equilibrium constant K/eg. The latter were obtained as follows: A dry septumed vial was charged with about 0.8 g. of dry acetonitrile and then equimolar amounts (about $2.7 \times 10^{-3}$ mols) of A and B were added. Samples were periodically removed from the mixture for gas liquid chromatography analysis. The entire operation was carried out at ambient temperature. The weight of product was calculated by the formula: weight of product = $(A/A_i) \times (W_i/W)$ where $A_i$ is the area of the compound, $A$ was the area of the acetonitrile, $W_i$ was the weight of the compound and $W$ was the weight of the acetonitrile.

The gas liquid chromatograms were taken on an Infotronics Model 2400 Series gas chromatograph equipped with a Model 68 linear temperature programmer and a 6 ft. by ⅛ inch (182.88 cm. by 3.18 mm) packed with diatomaceous earth of 100 to 120 mesh coated with 5% by weight of a trifluoropropylmethyl siloxane of 10,000 cs viscosity (designated SP-2401 by Supelco Incorporated). The injection port temperature was maintained at 200° C and the detector (He) at 310° C. The column was linearly programmed at 20° C/min. from 100° to 200° C with a chart speed of 2 min./inch. (2.45 cm).

Runs 2 to 5 are for purpose of comparison.

| Run No. | Silylamide A | $K_{eg}$* |
|---|---|---|
| (1) | Me$_3$SiN(t-Bu)—C(O)Me | 110.00 |
| (2) | (Me$_3$Si)$_2$NCMe (BSA) | 22.00 |
| (3) | Me$_3$SiN(Bu)—C(O)Me | 1.00 |
| (4) | Me$_3$SiN(Me)—C(O)Me | 0.30 |
| (5) | Me$_3$SiN(iPr)—C(O)Me | 0.00093 |

*$K_{eg}$ was calculated by the formula $K_{eg} = \frac{(C)(D)}{(A)(B)} = \frac{D^2}{B^2} = \frac{D^2}{(B-D)^2}$ This data shows that the N-t-butyltrimethylsilylacetamide of this invention is 5 times faster than the best previously known silylating agent (2); is 110 times faster than the corresponding n-butyl compound (3); is 366 times faster than the N-methyl compound (4); and is 100,000 times faster than the N-isopropyl derivative (5).

EXAMPLE 3

Into a dry flask equipped with a stirrer, distillation head and septum was added 5 g. of freshly distilled $$Me_3SiN(t\text{-}Bu)-C(O)Me$$

and 1.72 g. of freshly distilled dimethyldichlorosilane.

The system was evacuated at ambient temperature and trimethylchlorosilane was removed at ambient temperature. The product $$Me_2Si\{N(t\text{-}Bu)-C(O)Me\}_2$$

was obtained in 91 percent yield. The product was reacted with methanol at room temperature and the amount of dimethyldimethoxysilane and t-butylacetamide produced were determined by infrared and nmr analysis. This procedure showed the product to be pure.

EXAMPLE 4

Using the procedure of Example 1, the following compounds can be prepared by reacting the following silanes with the following N-t-butylamides.

| Silane | N-t-butylamide | product |
|---|---|---|
| PhMe$_2$SiCl | t-Bu(H)NCEt | PhMe$_2$SiN(t-Bu)—C(O)Et |
| EtMe$_2$SiCl | t-Bu(H)NCMe | EtMe$_2$SiN(t-Bu)—C(O)Me |
| ViMe$_2$SiCl | t-Bu(H)NCMe | ViMe$_2$SiN(t-Bu)—C(O)Me |
| (CF$_3$CH$_2$CH$_2$)Me$_2$SiCl | t-Bu(H)NCMe | (CF$_3$CH$_2$CH$_2$)Me$_2$SiN(t-Bu)—C(O)Me |

That which is claimed is:

1. A composition of the formula $$R_nSi\{N(t\text{-}Bu)-C(O)R'\}_{4-n}$$

where $n$ is 2 or 3, R is of the group methyl, ethyl, vinyl, phenyl or 3,3,3-trifluoropropyl, at least 2 R's being methyl when $n$ is 3 and R' is methyl or ethyl.

2. The composition of claim 1 where $n$ is 2.

3. The composition of claim 1 where $n$ is 3.

4. The composition of claim 1 of the formula $$Me_2Si\{N(t\text{-}Bu)-C(O)Me\}_2.$$

5. The compsoition of claim 1 of the formla $$Me_3SiN(t\text{-}Bu)-C(O)Me.$$

* * * * *

UNITED STATES PATENT AND TRADEMARK OFFICE
CERTIFICATE OF CORRECTION

PATENT NO. : 4,107,196

DATED : August 15, 1978

INVENTOR(S) : Cecil L. Frye and Thomas H. Lane

It is certified that error appears in the above-identified patent and that said Letters Patent are hereby corrected as shown below:

In Column 3, line 17; the word reading "reactive" should read "relative".

In Column 4, line 32; the headings reading

"Silane          N-t-butylamide product" should read

"Silane          N-t-butylamide       Product".

Signed and Sealed this

Third Day of November 1981

[SEAL]

Attest:

GERALD J. MOSSINGHOFF

*Attesting Officer*      *Commissioner of Patents and Trademarks*